United States Patent [19]

Groenen et al.

[11] Patent Number: 5,108,918
[45] Date of Patent: Apr. 28, 1992

[54] METHOD FOR IDENTIFYING AND USING BIOSYNTHETIC GENES FOR ENHANCED PRODUCTION OF SECONDARY METABOLITES

[75] Inventors: Martien A. M. Groenen, Leiderdorp; Annemarie E. Veenstra, Vennep; Pieter van Solingen, Naaldwijk; Bertus P. Koekman, Schipluiden, all of Netherlands

[73] Assignee: Gist-brocades, Delft, Netherlands

[21] Appl. No.: 305,532

[22] Filed: Feb. 1, 1989

[30] Foreign Application Priority Data

Aug. 11, 1988 [EP] European Pat. Off. ...... 88/201714.8
Sep. 28, 1988 [EP] European Pat. Off. ...... 88/202118.1

[51] Int. Cl.$^5$ .................... C12N 15/00; C12N 15/10; C12N 15/63
[52] U.S. Cl. .............................. 435/172.3; 435/252.3; 435/320.1
[58] Field of Search ...................... 435/69.1, 43, 172.3, 435/252.3, 435, 320; 935/14

[56] References Cited

FOREIGN PATENT DOCUMENTS 0225128 10/1987 European Pat. Off. .
0320272 6/1989 European Pat. Off. .

OTHER PUBLICATIONS

Biotechnology 5:494–497, May 1987, Cantoral et al., High-Frequency Transformation of Penicillium chrysocenum.
Trends in Biotechnology (5) 306–308, 1987, Martin, Cloning of Genes Involved in Penicillin and Cephalosporin Biosynthesis.
Martin and Liras, "Biosynthesis of β-Lactam Antibiotics: Design and Construction of Overproducing Strains" in Trends Biotechnol. (1985) 3(2):39–44.
Carr et al., "Cloning and Expression of the Isopenicillin N Synthetase Gene from Penicillium chrysogenum" in Gene (1986) 48:257–266.
Samson, et al., "Isolation, Sequence Determination and Expression in Escherichia coli of the Isopenicillin N Synthetase Gene from Cephalosporium acremonium" in Nature (1985) 318(14):191–194.
Skatrud, et al., "Strain Improvement Studies in Penicillium chrysogenum Using the Cloned P. chrysogenum Isopenicillin N Synthetase Gene and the amdS Gene of Aspergillus nidulans" in SIM News (1987) 37:77.
Maniatis, T., et al., "Molecular Cloning, a laboratory manual" in Cold Spring Harbor Laboratory (1985), pp. 227–228.
Sargent, T. D., et al., "Differential Gene Expression in Gastrula of Xenopus laevis" in Science (1983) 22:135–139.
Hedrick, et al., "Isolation of cDNA Clones Encoding T Cell-Specific Membrane-associated Proteins" in Nature (1984) 308:149–153.
Ramon, et al., "Cloning and Characterization of the Isopenicillin N Synthetase Gene Mediating the Formation of the beta-Lactam Ring in Aspergillus nidulans" in Gene (1987) 57:171–181.

Primary Examiner—David L. Lacey
Assistant Examiner—John D. Ulm

[57] ABSTRACT

Novel methods and compositions are provided for the enhanced production of secondary metabolites. Methods are provided for identifying sequences which when transformed into secondary metabolite producing hosts, enhance the production of secondary metabolite. The process is exemplified for penicillin. In addition, the P. chrysogenum acyltransferase gene is isolated and sequenced.

22 Claims, 14 Drawing Sheets

L-α-aminoapidipic acid + L-crysteine + L-valine

↓ Dipeptide Synthetase

δ-(L-α-aminoadipyl)-L-cysteine

↓ Tripeptide Synthetase

δ-(L-α-aminoadipyl)-L-cysteinyl-D-valine (LLD-ACV)

↓ Isopenicillin N Synthetase (IPNS)

Isopenicillin N (IPN)

↓ IPN: 6-APA amidohydrolase

6-Aminopenicillanic Acid (6-APA)

↓ Acyl-CoA.6-APA acyltransferase

Penicillin G or V

FIG. 1

```
         10        20        30        40        50        60
AAGCTTTCAGGCAACCTAGGCAACCCAATAGGAACCAAGTGATAGGCCCACCTGCTTTCT 70        80        90       100       110       120
ATCTAGTCTGGACGGTTGCTATTGGCTCGATCATTGTTTACCATCCCGGCAAAAAGCTCT 130       140       150       160       170       180
ACAGAGTTGTGCTATTTCTATTCCTGTCTTGGCATGTCCAGGCTGGCTGTTATCGCCTCC 190       200       210       220       230       240
GTGGTGAACCCTCTTCATGCAAGAGGTCAGTCAATAATGCGCTTCACCGTTCTCGACGAA 250       260       270       280       290       300
ACTTGGCATCCATGCTCAATCCAGCTCCTCGGCAAGACTAGGCGGATGCAGCAGGGATAC 310       320       330       340       350       360
TCGAGGTGCCCCAGTTGATGTCCCATCAGTGTCATGCTATGGTCCCAGATTGGTGGCTAC 370       380       390       400       410       420
GGCAATATAAATGTCAGCATGCAGTTCCGCCTGCATGATCATCCCCAGGACGCGTTTGTC 430       440       450       460       470       480
ATCTCCGTCAGCCAGGTCTCAGTTGTTTACCCATCTTCCGACCCGCAGCAGAAATGCTTC
                                                        MetLeuH 490       500       510       520       530       540
ACATCCTCTGTCAAGGCACTCCCTTTGAAGTAAGTGCTGCACTGAATACCAGATTTTTC
isIleLeuCysGlnGlyThrProPheGlu 550       560       570       580       590       600
CTTCTGAATCTTCCGAGTTCTGACCTGATCCAGATCGGCTACGAACATGGCTCTGCTGCC
                                    IleGlyTyrGluHisGlySerAlaAla 610       620       630       640       650       660
AAAGCCGTGATAGCCAGAAGCATTGACTTCGCCGTCGATCTCATCCGAGGGAAAACGAAG
LysAlaValIleAlaArgSerIleAspPheAlaValAspLeuIleArgGlyLysThrLys 670       680       690       700       710       720
AAGACGGACGAAGAGCTTAAACAGGTACTCTCGCAACTGGGGCGCGTGATCGAGGAAAGA
LysThrAspGluGluLeuLysGlnValLeuSerGlnLeuGlyArgValIleGluGluArg 730       740       750       760       770       780
TGGCCCAAATACTACGAGGAGATTCGCGGTGAGTGCCACTTCGGTCTTTCCTACATTTTC
TrpProLysTyrTyrGluGluIleArgG
```

FIG. 3A

```
        790       800       810       820       830       840
TGCACCAATGCTGACCGATGACCCCCGAAAAACCAGGTATTGCAAAGGGCGCTGAACGCG
                                      lyIleAlaLysGlyAlaGluArgA 850       860       870       880       890       900
ATGTCTCCGAGATTGTCATGCTTAATACCCGCACGGAATTTGCATACGGGCTCAAGGCAG
 spValSerGluIleValMetLeuAsnThrArgThrGluPheAlaTyrGlyLeuLysAlaA 910       920       930       940       950       960
CCCGTGATGGCTGCACCACTGCCTATTGTCAACTTCCAAATGGAGCCCTCCAGGGCCAAA
 laArgAspGlyCysThrThrAlaTyrCysGlnLeuProAsnGlyAlaLeuGlnGlyGlnA 970       980       990      1000      1010      1020
ACTGGGATGTACGTTAAGAGATTTTACCTCCTCATTTTATTCCATCGAATTTGCGCCGAC
snTrpAsp 1030      1040      1050      1060      1070      1080
TAATTTGGTTGTTCAAGTTCTTTTCTGCCACCAAAGAGAACCTGATCCGGTTAACGATCC
              PhePheSerAlaThrLysGluAsnLeuIleArgLeuThrIleA 1090      1100      1110      1120      1130      1140
GTCAGGCCGGACTTCCCACCATCAAATTCATAACCGAGGCTGGAATCATCGGGAAGGTTG
rgGlnAlaGlyLeuProThrIleLysPheIleThrGluAlaGlyIleIleGlyLysValG 1150      1160      1170      1180      1190      1200
GATTTAACAGTGCGGGGGTCGCCGTCAATTACAACGCCCTTCACCTTCAGGGTCTTCGAC
lyPheAsnSerAlaGlyValAlaValAsnTyrAsnAlaLeuHisLeuGlnGlyLeuArgP 1210      1220      1230      1240      1250      1260
CCACCGGAGTTCCTTCGCATATTGCCCTCCGCATAGCGCTCGAAAGCACTTCTCCTTCCC
roThrGlyValProSerHisIleAlaLeuArgIleAlaLeuGluSerThrSerProSerG 1270      1280      1290      1300      1310      1320
AGGCCTATGACCGGATCGTGGAGCAAGGCGGAATGGCCGCCAGCGCTTTTATCATGGTGG
lnAlaTyrAspArgIleValGluGlnGlyGlyMetAlaAlaSerAlaPheIleMetValG 1330      1340      1350      1360      1370      1380
GCAATGGGCACGAGGCATTTGGTTTGGAATTCTCCCCCACCAGCATCCGAAAGCAGGTGC
lyAsnGlyHisGluAlaPheGlyLeuGluPheSerProThrSerIleArgLysGlnValL 1390      1400      1410      1420      1430      1440
TCGACGCGAATGGTAGGATGGTGCACACCAACCACTGCTTGCTTCAGCACGGCAAAAATG
euAspAlaAsnGlyArgMetValHisThrAsnHisCysLeuLeuGlnHisGlyLysAsnG 1450      1460      1470      1480      1490      1500
AGAAAGAGCTCGATCCCTTACCGGACTCATGGAATCGCCACCAGCGTATGGAGTTCCTCC
luLysGluLeuAspProLeuProAspSerTrpAsnArgHisGlnArgMetGluPheLeuL 1510      1520      1530      1540      1550      1560
TCGACGGGTTCGACGGCACCAAACAGGCATTTGCCAGCTCTGGGCCGACGAAGACAATTA
euAspGlyPheAspGlyThrLysGlnAlaPheAlaSerSerGlyProThrLysThrIleI 1570      1580      1590      1600      1610      1620
TCCCTTTAGCATCTGCCGCGCTTACGAGGAGGGCAAGAGCAGAGGCGCGACTCTGTTCAA
leProLeuAlaSerAlaAlaLeuThrArgArgAlaArgAlaGluAlaArgLeuCysSerI
```

FIG. 3B

```
          1630       1640       1650       1660       1670       1680
TATCATCTACGACCATGCCCGTAGAGAGGCAACGGTGCGGCTTGGCCGGCCGACCAACCC
 leSerSerThrThrMetProValGluArgGlnArgCysGlyLeuAlaGlyArgProThrL 1690       1700       1710       1720       1730       1740
TGATGAGATGTTTGTCATGCGGTTTGACGAGGAGGACGAGAGGTCTGCGCTCAACGCCAG
 euMetArgCysLeuSerCysGlyLeuThrArgArgThrArgGlyLeuArgSerThrProG 1750       1760       1770       1780       1790       1800
GCTTTGAAGGCTCTTCATGACGAGCCAATGCATCTTTTGTATGTAGCTTCAACCGACTCC
 lyPheGluGlySerSerEnd 1810       1820       1830       1840       1850       1860
GTCTTCACTTCTTCGCCCGCACTGCCTACCGTTTGTACCATCTGACTCATATAAATGTCT 1870       1880       1890       1900       1910       1920
AGCCCCTACCTACACTATACCTAAGGGAGAGAAGCGTAGAGTGATTAACGTACGGGCCTA 1930       1940       1950       1960       1970       1980
TAGTACCCCGATCTCTAGATAGAACATTTAGTAGAGATTAGGATGCCTAACTAATTTAAC 1990       2000       2010       2020       2030       2040
TTGAGCATTGTCCCGTTCATATTGATTTTCAGTCCATTATACACTCTTAATCGTTTCCCG 2050       2060       2070       2080       2090       2100
GTAGAAGCCTGATATATACGACCATAGGGTGTGGAGAACAGGGCTTCCCGTCTGCTTGGC 2110       2120       2130       2140       2150       2160
CGTACTTAAGCTATATATTCTACACGGCCAATACTCAATGTGCCCTTAGCACCTAAGCGG 2170       2180       2190       2200       2210       2220
CACTCTAGGGTAAGTGCGGGTGATATAGGTGAGAAGTCTTAAGACTGAAGACAGGATATC 2230       2240       2250       2260       2270       2280
ACGCGTTACCCTGCACCGTACCTACTACCTTCAATATCAACTCTTTCAGGATGGACAGGG

TCGAC
```

FIG. 3C

```
        10         20         30         40         50         60
AAGCTTGAATCTCTATGTCTGATGAGACTATGTATTGTATATCAACTGCAACGTATCCGT 70         80         90        100        110        120
ATATGCGCACACGTTCGAAGGTCAAGGCCGTGGGGTCCACTGTGGCAGAAAAGTCCCGAT 130        140        150        160        170        180
TGTCTTCGATTCGAACTTGCTGCTATTATTCTACTTTGGACGTCAAGAAGGCAATTACAA 190        200        210        220        230        240
TCATATCCTAGAAGGATTTGTCATTTGATTCACTTCCCTCTTAAAATCTCAAAATCACAT 250        260        270        280        290        300
ACCCAATACATTACCATCTCTTCACCCCGCCAACCCCGCCATGTCCTCCAAGTCGCAATT
                                         MetSerSerLysSerGlnLe 310        320        330        340        350        360
GACCTACACGGCCCGCGCCCAATCGCACCCCAATCCCCTCGCGCGCAAGCTATTCCAAGT
uThrTyrThrAlaArgAlaGlnSerHisProAsnProLeuAlaArgLysLeuPheGlnVa 370        380        390        400        410        420
CGCCGAAGAGAAGAAGAGCAATGTTACTGTCTCCGCTGACGTGACCACAACAAAGGAGCT
lAlaGluGluLysLysSerAsnValThrValSerAlaAspValThrThrThrLysGluLe 430        440        450        460        470        480
CCTGGACCTCGCCGACCGTAAGTGAACCCAGCTCCCCCCACTCCAAAGGAACAAGCCACT
uLeuAspLeuAlaAspA 490        500        510        520        530        540
AACCATCCACAGGCCTTGGCCCCTACATCGCCGTGATTAAAACACACATCGACATCCTCT
            rgLeuGlyProTyrIleAlaValIleLysThrHisIleAspIleLeuS 550        560        570        580        590        600
CCGACTTCAGCCAAGAAACAATCGATGGCCTGAACGCCCTAGCGCAAAAGCACAACTTCC
erAspPheSerGlnGluThrIleAspGlyLeuAsnAlaLeuAlaGlnLysHisAsnPheL 610        620        630        640        650        660
TTATCTTCGAAGACCGCAAATTCATCGACATCGGCAACACAGTCCAGAAACAGTACCACA
euIlePheGluAspArgLysPheIleAspIleGlyAsnThrValGlnLysGlnTyrHisA 670        680        690        700        710        720
ATGGCACCCTCCGCATCTCCGAATGGGCGCACATAATCAACTGCTCCATCCTACCCGGCG
snGlyThrLeuArgIleSerGluTrpAlaHisIleIleAsnCysSerIleLeuProGly 730        740        750        760        770        780
AGGGCATTGTCGAGGCCCTCGCTCAAACCGCCCAGGCCACTGATTTCCCCTACGGCTCCG
luGlyIleValGluAlaLeuAlaGlnThrAlaGlnAlaThrAspPheProTyrGlySerG
```

FIG. 4A

```
           790       800       810       820       830       840
AGCGTGGCCTCCTCATCCTCGCCGAGATGACCTCGAAGGGATCCCTCGCAACAGGCGCCT
luArgGlyLeuLeuIleLeuAlaGluMetThrSerLysGlySerLeuAlaThrGlyAlaT 850       860       870       880       890       900
ACACCTCCGCCTCCGTCGACATCGCGCGCAAGTACCCCAGCTTCGTGCTTGGCTTTGTCT
yrThrSerAlaSerValAspIleAlaArgLysTyrProSerPheValLeuGlyPheValS 910       920       930       940       950       960
CGACCCGGTCTCTCGGCGAGGTCGAGTCTACAGAGGCGCCCGCGAGCGAGGATTTCGTCG
erThrArgSerLeuGlyGluValGluSerThrGluAlaProAlaSerGluAspPheValV 970       980       990      1000      1010      1020
TCTTCACCACTGGCGTCAACCTCTCGTCTAAGGGCGATAAGCTCGGTCAGCAGTACCAGA
alPheThrThrGlyValAsnLeuSerSerLysGlyAspLysLeuGlyGlnGlnTyrGlnT 1030      1040      1050      1060      1070      1080
CGCCGCAGTCGGCTGTTGGCCGCGGTGCTGACTTTATTATCTCTGGTCGTGGTATCTATG
hrProGlnSerAlaValGlyArgGlyAlaAspPheIleIleSerGlyArgGlyIleTyrA 1090      1100      1110      1120      1130      1140
CCGCTGCCGATCCTGTTGAGGCCGCTAAGCAGTACCAGCAGCAGGGCTGGGAGGCGTATC
laAlaAlaAspProValGluAlaAlaLysGlnTyrGlnGlnGlnGlyTrpGluAlaTyrL 1150      1160      1170      1180      1190      1200
TGGCCCGCGTGGGTGCGCAATAGGAGCGTGCGTCCACCTTCCACTATAGGTACATTTGTG
euAlaArgValGlyAlaGlnEnd 1210      1220      1230      1240      1250      1260
TTGATGCATAATGAGAATTCTATATACGATGTCGTGCTATAACCTTTTGCAGTTTGGTGC 1270      1280      1290      1300      1310      1320
TTCCTTACATCACCGGTGTTCACGACCTCGGGACCTCGGGACCTCCCGATGCCTTTCCAG 1330      1340      1350      1360      1370      1380
GGCCATGTAAGGGCTTTCTGGCATGTACAGACGGTGCAAGGGCAAGGTTGAGTCAACATA 1390      1400
CATGCAAGTGCTCAGCGGCATGT
```

FIG. 4B

```
        10        20        30        40        50        60
CTATGAATTCCCATCAGTAGAGGCCAATTCCCGAGAATTTCCCGATTCCGAGGCTAAAGA 70        80        90       100       110       120
GGCTAAAGAGGACCTCCATGGCCCGGCCTTCCCCGTATCAACGCGGGCAGCTCTGACATC 130       140       150       160       170       180
AGTCCCGCGTCAGCCCGATCAGTTCTCCGGGATACTCGGTACGGCGTCTGAGGTACTGCT 190       200       210       220       230       240
TTTATAGATATACCTAGGAAAAGAGGGATTGCATCATACTTCGAGCAAGTACCTTATTCC 250       260       270       280       290       300
GTCGAATACATCATCGGGAGGTACCTGGGTTGCTACGGTTGCGACCTCTTCACCGGCCTG 310       320       330       340       350       360
CCCCACCAAAACTGACCCCTCCACTCTTTACTGATCGCGACTCACCGTGGCCTGATTAGT 370       380       390       400       410       420
TCTTTCTCCTTCTTCTATCCCTTTTCTTGCTCCTTTCACCATTGTCATACCATTAACTAC

CCACA
```

FIG. 5

METHOD FOR IDENTIFYING AND USING BIOSYNTHETIC GENES FOR ENHANCED PRODUCTION OF SECONDARY METABOLITES

INTRODUCTION

1. Technical Field

The subject field concerns the isolation and use of genes for the production of secondary metabolites.

2. Background and Relevant Literature

As a result of classical strain improvements, penicillin production has increased enormously over the last four decades. These classical strain improvements were primarily based on random mutagenic treatments of *Penicillium chrysogenum* and subsequent selection for mutants that produced more penicillin. The development of cloning techniques however has added a potentially powerful new tool to further improve penicillin production in this fungus.

Penicillin is produced in the filamentous fungus *P. chrysogenum* in several enzymatic steps from α-aminoadipic acid, cysteine and valine (see FIG. 1). At present it is not clear whether the amidohydrolase and the acyltransferase are encoded by two separate enzymes encoded by two different genes or one enzyme has both activities. It is also not clear which enzymatic reaction(s) is (are) rate-limiting in the process of penicillin biosynthesis and whether regulatory proteins are involved.

Until recently, the gene of only one of the enzymes active in the biosynthetic pathway to penicillin G, the isopenicillin N synthetase (IPNS) or cyclase, had been cloned and sequenced (Carr et al., *Gene* (1986) 48:257-266), using the corresponding *Acremonium chrysogenum* gene (Samson et al., *Nature* (1985) 318:191-194). The latter gene was cloned and identified by purifying the IPNS protein, determining the amino-terminal amino acid sequence, preparing a set of synthetic oligodeoxyribonucleotides according to this sequence and probing a cosmid genomic library with these mixed oligodeoxyribonucleotides (Samson, vide supra).

Strain improvement studies using the cloned *Penicillium chrysogenum* isopenicillin N synthetase genes in *Penicillium chrysogenum* resulted in enhanced enzyme activity, but no improvement in penicillin production, nor in IPNS rate limiting (Skatrud et al., Poster presentation 1987 Annual meeting of *Society of Industrial Microbiology*, Baltimore, Aug. 1987, abstract published in SIM News (1987) 37:77).

It has been documented that the biosynthesis of β-lactam antibiotics is subject to glucose repression (Martin and Liras, *TIBS* (1985) 3:39-44). However, it is not known whether this regulation is exerted on the transcriptional or translational level.

If the former regulation applies, differences in mRNA levels between producing and non-producing cultures may be employed to isolate the said genes. There is the further uncertainty of levels of the mRNAs encoding the various enzymes in penicillin producing cells.

SUMMARY OF THE INVENTION

Subtraction isolation methods are employed for identifying genes associated with the production of secondary metabolites in microorganisms. The method is exemplified with production of penicillin in *P. chrysogenum*.

BRIEF DESCRIPTION OF THE DRAWINGS

FIG. 1

The biosynthetic pathway to penicillin G or V in *P. chrysogenum* is shown schematically.

Figure 2A:
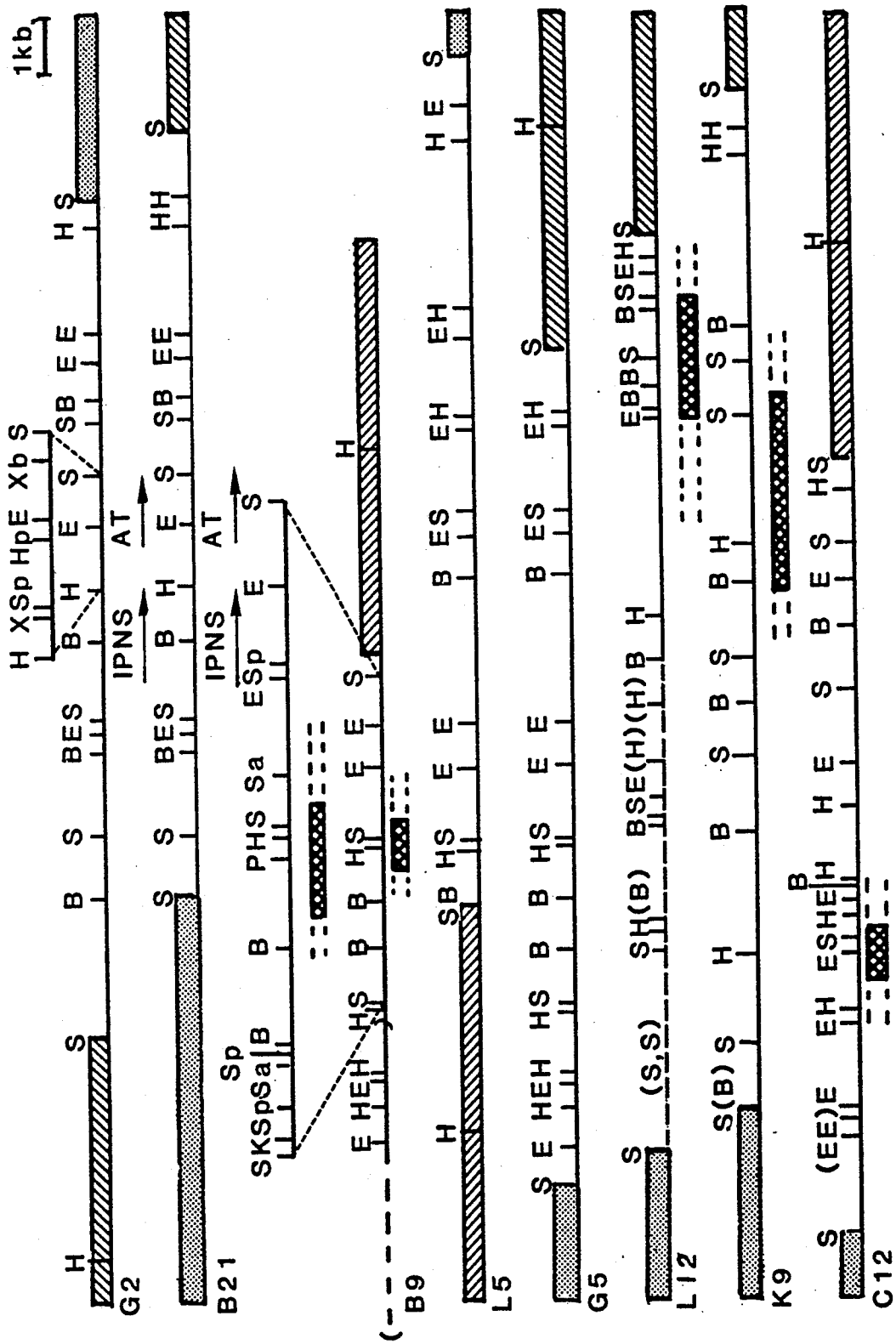
Figure 2B:
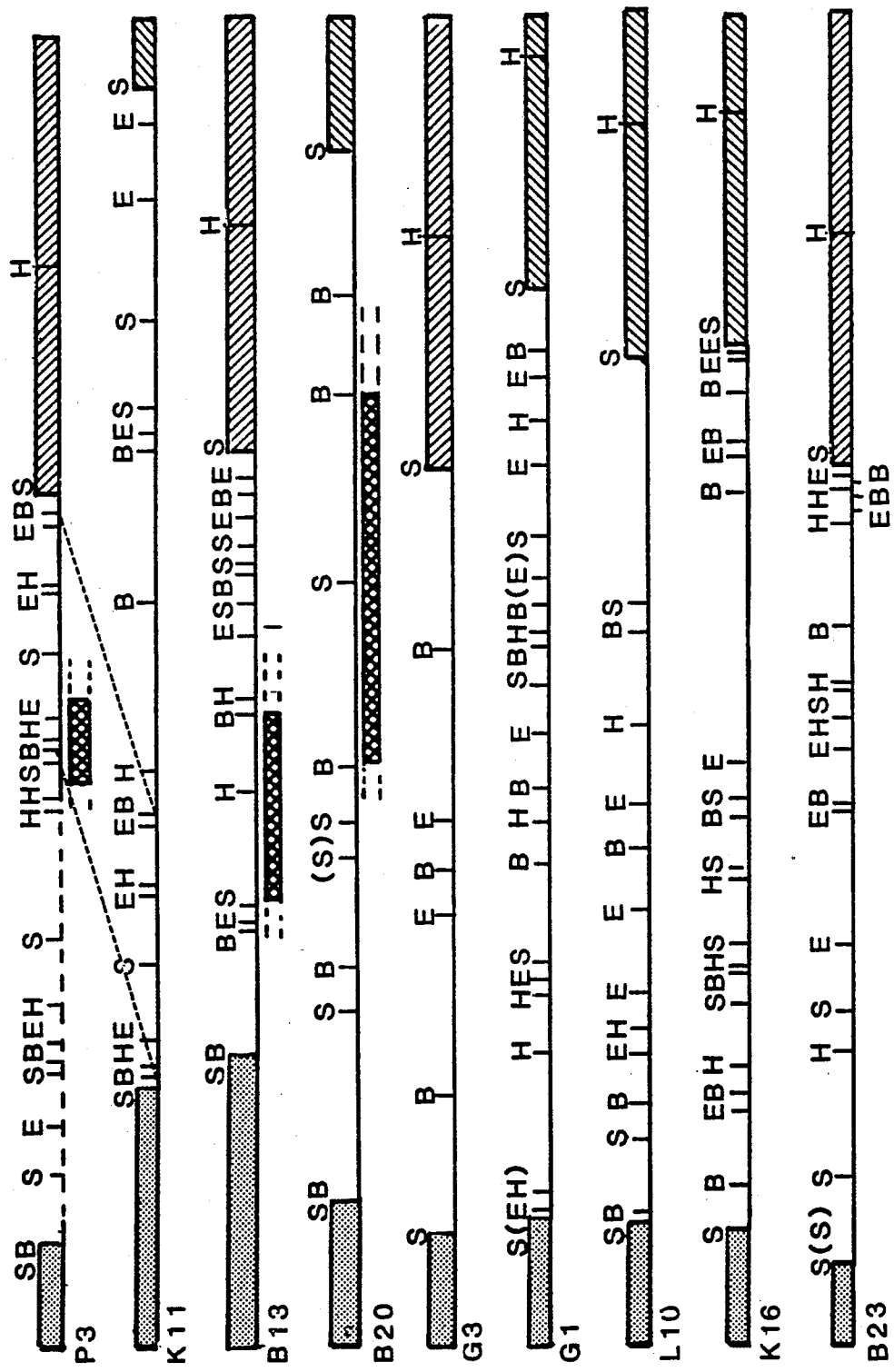

FIGS. 2A and 2B

Physical map of lambda clones isolated by the method of this invention. Clones lambda G2 and lambda B21 contain the cyclase acyltransferase gene cluster Clones lambda B9, G5 and L5 contain the cryptic gene Y. Other lambda clones contain other cryptic genes.

E = EcoRI;  B = BamHI;  H = HindIII;  K = KpnI;

S = SalI;  Sa = SacI;  Sp = SphI;  P = PstI;

X = XhoI;  Xb = XbaI;  Hp = HpaI;  N = NcoI and

Bg = BglII

The diagonally hatched line = right arm of bacteriophage lambda EMBL3 (9 kb)
The stippled line = left arm of bacteriophage lambda EMBL3 (20.3 kb)
THe cross hatched line = region that hybridizes to pen+ cDNA
The broken line = unclear region of map
Parenthesis = position/occurrence of restriction site not clear;
la and ra are left arm and right arm respectively of bacteriophage lambda.

FIG. 3

Nucleotide sequence and deduced amino acid sequence of the *P. chrysogenum* acyltransferase gene.

FIGS. 4A and 4B

Nucleotide sequence and deduced amino acid sequence of the *P. chrysogenum* pyrG gene. This sequence forms the major part of the 2.4 kb EcoRI fragment that acts as a transformation stimulating sequence.

FIG. 5

Nucleotide sequence of the promoter of the *P. chrysogenum* phosphoglycerate kinase gene.

FIG. 6

A restriction site and functional map of pUC13::pyrG.

FIG. 7

A restriction site and functional map of pPS54.

FIG. 8

A restriction site and functional map of pRH05.

FIG. 9

A restriction site and functional map of pGJ01 A and B.

FIG. 10

A restriction site and functional map of pPS47.

DESCRIPTION OF THE SPECIFIC EMBODIMENTS

In accordance with the subject invention, DNA fragments are identified which include sequences which are mono-or polycistronic. The gene(s) encoded by the sequences are translated to enzymes concerned with the production of secondary metabolites. These sequences of interest are identified by comparison of DNA sequences isolated from an organism competent to produce the secondary metabolite, where the genes of interest are actively expressed, and a microorganism in which expression is silent. The absence of expression may be as a result of lack of induction or repression of gene expression, mutation, or other event which results in transcriptional silence of the gene(s) of interest. The DNA which is isolated may be as a result of screening a gene library, either genomic or cDNA library. By employing a cDNA probe enriched for sequences expressed during the biosynthesis of secondary metabolites, positive hybrids may be identified in the library for subsequent manipulation to provide for expression constructs for the enzyme(s) associated with the production of the secondary metabolite.

The identified DNA sequences will comprise at least one gene encoding an antibiotic biosynthetic enzyme and/or a regulatory protein of this biosynthetic pathway. The sequence when employed as an expression cassette and transformed into a suitable host microorganism will result in increased production of the secondary metabolite, providing for higher yields of the secondary metabolite. This method is exemplified by and finds particular application with β-lactam producing microorgansims for the production of antibiotics, particularly penicillins. Preferably, the expression cassette will include genes encoding enzymes that catalyze rate-limiting steps or genes encoding regulatory proteins for induction of transcription.

The subject method further provides sequences for which the encoded product is not known, but the sequence is found to provide an enhanced yield of a desired product. These sequences are referred to as "cryptic genes," which means sequences obtainable by isclation methods described herein, which sequences encompass genes for which no known function is assignable. These genes are characterized by being dosed and/or expressed in higher amounts in the transformed host-microorganisms as compared with their untransformed hosts. In addition to the "cryptic genes," other genes provided are IPNs; 6-EPA amidohydrolase or acyltransferase. A cryptic gene identified as "Y" was shown to provide enhanced biosynthesis of penicillin.

The microorganisms employed in the subject invention include both prokaryotes and eukaryotes, including bacteria such as those belonging to the genus *Actinomycetes*, or fungi, belonging to the genera *Aspergillus, Acremonium* or *Penicillium*.

Depending upon the source of the fragment, either genomic or cDNA, either prokaryotic or eukaryotic, various expression cassettes may be constructed. With genomic DNA from a bacterium, the fragment containing a mono-or polycistronic coding region may include its own transcriptional initiation regulatory region, as well as a transcriptional initiation termination region and appropriate translational signals, e.g. Shine-Dalgarno sequence and stop codons. Where the genomic DNA is from a fungus, normally only one gene will be associated with a transcriptional initiation regulatory region, so that each gene will have its own independent transcriptional initiation regulatory region. Where cDNA is employed, it will be necessary to provide an appropriate transcriptional initiation regulatory region.

The genes of interest may be obtained at random from a gene library (e.g., genomic or cDNA library) of a high-yielding β-lactam producing strain or its wild-type ancestor, or may be selected among a subset of the library which contains genes which may be rate-limiting in antibiotic biosynthesis. Particularly valuable genes include those which are specifically expressed during antibiotic biosynthesis, including the genes encoding β-lactam biosynthetic enzymes known in the art, e.g. tripeptide synthetase, cyclase (IPNS), transacylase, epimerase, expandase, hydroxylase, transacetylase. Preferably genes encoding IPN:6-APA amidohydrolase or acyltransferase are dosed or expressed in higher amounts resulting in higher yields of the desired antibiotic in the transformed fungus.

It will be appreciated by those skilled in the art, that the gene(s) to be expressed in a β-lactam producing host may either carry its own native promoter sequence which is recognized by an RNA polymerase of the host cell, or may be ligated to any other suitable promoter, e.g. that of a different β-lactam biosynthetic gene or that of a glycolytic gene such as phosphoglycerate kinase, glyceraldehyde phosphate dehydrogenase, triose phosphate isomerase, or that of the translational elongation factor, Ef-Tu, or the like.

Such a promoter may be employed to influence regulation of expression of one or more genes encoding said enzymes. This will lead to an increased production of the antibiotic after transformation, since penicillin production is now also possible under conditions that in the untransformed host strain do not lead to penicillin production, e.g. glycolytic enzymes are expressed in the presence of glucose, while the production of penicillin, on the other hand, is repressed in the presence of glucose (Martin, vide supra). By bringing the expression of penicillin biosynthetic genes under the control of a promoter of a glycolytic gene, the genes can also be expressed in the presence of glucose and hence penicillin can be produced early in the fermentation, when a high concentration of glucose is required for the generation of a sufficient amount of mycelium.

The present invention exemplifies the promoter of the phosphoglycerate kinase gene of *P. chrysogenum* as a promoter to be used to overcome glucose repression of penicillin biosynthesis. This promoter was isolated from a genomic library of *P. chrysogenum* by standard methods, using oligodeoxyribonucleotides probes derived from the published yeast sequence of Hitzeman et al., *Nucleic Acids Res.* (1982) 10:7791–7808. The nucleotide sequence of the phosphoglycerate kinase promoter is specified in FIG. 5.

For transformation of Penicillium, constructs are employed including at least one marker for selection of transformed cells and, preferably, for enhancing maintenance of the integrated DNA. Therefore, the vector preferably includes a DNA sequence known to enhance transformation efficiencies. An example of such a DNA sequence is the "ans"-element, isolated from *Aspergillus nidulans* (cf. Ballance and Turner, *Gene* (1985) 36:321-331). The present invention provides a DNA sequence, isolated from the genome of *P. chrysogenum*, that has been identified as a sequence with an effect similar to the effect of the "ans" sequence. Since this sequence is native to *P. chrysogenum*, it can be used to increase transformation efficiencies in *P. chrysogenum*. The DNA sequence encompasses the *P. chrysogenum* pyrG gene and can be used either alone or in combination with a pyrG-host, in which case the DNA sequence provides both the selection for transformants and the transformation enhancing effect (cf. EP-A-260762), or in combination with another selection marker, e.g. a gene encoding resistance to a biocide, such a phleomycin. In the latter case selection for transformants and the transformation enhancing effect are provided by two separate DNA sequences and the sole function of the pyrG element is to enhance transformation frequencies. Only an efficiency enhancing fragment need be employed, usually at least about 20% of the sequence of FIG. 4.

Useful markers for the selection of transformant clones may be homologous or heterologous biosynthetic genes capable of complementing an auxotrophic requirement of the host cell, caused by a defect in a metabolic route to an amino acid, e.g. arginine, a nucleotide precursor, e.g. uracil, and the like.

The structural gene providing the marker for selection may be native to the wild-type Penicillium host or a heterologous structural gene which is functional in the host. For example, structural genes coding for an enzyme in a metabolic pathway may be derived from Penicillium or from other filamentous fungi, e.g. Aspergillus, Neurospora, Podospora, or yeasts, where the structural gene is functional in the Penicillium host and complements the auxotrophy to prototrophy for the genetic capability.

The complementing structural gene may be derived from a metabolic pathway, such as the synthesis of purines or pyrimidines (nucleosides) or amino acids. Of particular interest are structural genes encoding enzymes in the pyrimidine pathway, e.g. the gene encoding the enzyme orotidine-5'-phosphate decarboxylase (pyrG or pyr4). Other genes of interest are amino acid biosynthetic genes, e.g. ornithine carbamoyl transferase (argB) and arginine succinate lyase (arg4).

Instead of auxotrophic markers, fermentation markers may be used, such as the capability of using amides as a sole source of carbon or nitrogen, growth on various sugars, e.g. galactose, or the like.

Furthermore, genes encoding resistance to biocides may be used, such as hygromycin, gentamicin, phleomycin, glyphosate, bialaphos, and the like.

Constructs will be provided comprising the sequence of interest, and may include other functions, such as replication systems in one or more hosts, e.g. cloning hosts and/or the target host for expression of the secondary metabolite; one or more markers for selection in one or more hosts, as indicated above; genes which enhance transformation efficiency; or other specialized function.

The construct will contain at least one gene isolated by the method of this invention. The construct may be prepared in conventional ways, by isolating other desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various fragments may be combined, cloned, isolated and sequenced in accordance with conventional ways. After each manipulation, the DNA fragment or combination of fragments may be inserted into the cloning vector, the vector transformed into a cloning host, e.g. E. coli, the cloning host grown up, lysed, the plasmid isolated and the fragment analyzed by restriction analysis, sequencing, combinations thereof, or the like.

Various vectors may be employed during the course of development of the construct and transformation of the host cell. These vectors may include cloning vectors, expression vectors, and vectors providing for integration into the host or the use of bare DNA for transformation and integration.

The cloning vector will be characterized, for the most part, by a marker for selection of a host containing the cloning vector and a transformation stimulating sequence, may have one or more polylinkers, or additional sequences for insertion, selection, manipulation, ease of sequencing, excision, or the like.

Expression vectors will usually provide for insertion of a construct which includes the transcriptional and translational initiation and termination regions; alternatively the construct may lack one or both of the regulatory regions, which will be provided by the expression vector upon insertion of the sequence encoding the protein product.

The DNA encoding enzyme(s) of interest may be introduced into a Penicillium host in substantial accordance with the procedure as described in EP-A-260762.

Efficient transformation of Penicillium is provided to produce transformants having one or more structural genes capable of expression, particularly integrated into the host genome (integrants). DNA constructs are prepared which allow selection of transformed host cells. Conditions are employed for transformation which result in a high frequency of transformation, so as to ensure selection and isolation of transformed hosts expressing the structural gene(s) of interest. The resulting transformants provide for stable maintenance and expression of the integrated DNA.

The genes of interest to be introduced by transformation may form an integral part of the transformation vector, but it will often be more convenient to offer these genes on a separate vector in the transformation mixture, thus introducing the said genes by cotransformation along with the selective vector, which is a fairly efficient process in filamentous fungi (Punt et al., Gene (1987) 56:117–124; K Wernars et al., Mol. Gen. Genet. (1987) 209:71–77; I. E. Mattern et al., Mol. Gen. Genet. (1987) 210:460–461.

As a result of the transformation, there will be at least one copy of the gene(s) of interest frequently two or more, usually not exceeding about 100, more usually not exceeding about 10. The number will depend upon whether integration or stable episomal maintenance is employed, the number of copies integrated, whether the subject constructs are subjected to amplification, and the like.

The subject invention exemplifies a method to isolate genes involved in penicillin biosynthesis from a gene library of the producing organism, P. chrysogenum, using specific cDNA probes which method is paradigmatic for identifying cryptic genes for the enhanced production of secondary metabolites. This method for the isolation of DNA constructs encoding one or more genes that take part in the biosynthesis of secondary metabolites, comprises the screening of a gene library with a cDNA probe enriched for sequences specifically expressed during the biosynthesis. By "specifically" expressed is meant that expression of these genes is silent or at a very low level (for example less than 5% of production level) in the absence of penicillin production and in contrast is high during penicillin production. To this end, radioactive or other labeled cDNA probes are synthesized on mRNA templates isolated from *P. chrysogenum* mycelia during the penicillin production phase.

The probes are then enriched for the desired genes by eliminating the genes that hybridize to an mRNA preparation derived from a Penicillum fermentation under conditions not allowing penicillin production, e.g. high glucose concentration. Using this enriched probe, clones are selected from a *P. chrysogenum* gene library that do not hybridize to a probe derived from non-producing mycelia. A large number of the clones thus isolated appear to encode the penicillin biosynthetic enzyme isopenicillin N-synthetase (IPNS or cyclase).

Furthermore, among the clones, several copies of the gene encoding the side-chain exchanging enzyme (acyltransferase) are found to be present, for which a DNA probe was constructed, using the amino-terminal peptide sequence of the purified enzyme. The identity of these clones is biochemically and biologically verified. The nucleotide and deduced amino acid sequence of the acyltransferase gene are specified in FIG. 3. Surprisingly, the genes encoding the isopenicillin N-synthetase and acyltransferase enzymes are present together on one DNA fragment. This was demonstrated by hybridization of a genomic library of *P. chrysogenum* in the lambda vector EMBL 3 with separate probes, specific for each of these genes. Identical clones hybridize separately with both probes.

Moreover, after construction of a physical map of one genomic lambda clone, and hybridization of restriction digests of the lambda clone with separate probes for both of the genes, the genomic organization was shown to be such as depicted in FIG. 2 (clones B21 and G2). The presence of both genes on one large DNA fragment allows construction of *P. chrysogenum* strains with a higher dosage of both the isopenicillin N-synthetase and acyltransferase genes, without disturbing the relative organization or the balanced expression of both genes. Moreover, the introduction of multiple copies of the large DNA fragment allows expression of both genes on the DNA fragment in their natural environment with upstream and downstream sequences that are identical to the normal situation.

Both the balanced expression and the maintenance of the natural environment prove to be beneficial for the efficiency of gene expression and hence of penicillin production. The isolation techniques of the isopenicillin N-synthetase plus acyltransferase gene cluster may be advantageously applied for the isolation of other penicillin biosynthetic genes by chromosome walking techniques, where the penicillin biosynthetic genes may be clustered.

Furthermore, a number of cryptic genes have been isolated, to which no function has been assigned but which are likely to play a part in β-lactam biosynthesis. A physical map of the cryptic genes of the invention is provided in FIGS. 2a and 2b (clones B9-B23).

Of these "cryptic" genes, the gene designated Y, present on clones B9, L5 and G5, when transformed (on a 3.0 kb SphI+BamHI subfragment) to a suitable host, stimulates the production of penicillin by 26%, compared to the untransformed host. This demonstrates the involvement of the product of gene Y in penicillin biosynthesis. Moreover, this demonstrates that transformation using genes isolated by the method of the invention, without knowing their function or identity, can be applied successfully in strain improvement of *P. chrysogenum*.

The present invention is further exemplified by transforming *Penicillium chrysogenum* with genes that are specifically expressed under conditions where the antibiotic is synthesized, and which encode gene products catalyzing biosynthetic reactions leading to the antibiotics.

One such enzyme, acyltransferase (hereinafter referred to as AT), catalyzes the final step in penicillin biosynthesis, i.e. the exchange of the aminoadipyl moiety of isopenicillin N with a hydrophobic acyl side chain precursor, e.g. phenylacetic or phenoxyacetic acid, thus yielding penicillin G or V, respectively.

The acyltransferase gene of *P. chrysogenum* is provided, including the nucleic acid sequence, conservative mutations, where the sequence encodes the same amino acid sequence, but may have as many as 30% different bases, more usually not more than about 10% different bases, or mutations which are non-conservative, where fewer than about 10%, more usually fewer than about 5%, and preferably not more than about 1% of the amino acids are substituted or deleted, and there are fewer than 5% of inserted amino acids, where the percent is based on the number of naturally occurring amino acids. In addition, fragments of both the nucleic acid encoding the enzyme, usually at least about 9 codons, more usually at least about 15 codons may be employed, as well as their expression products, as probes, for the production of antibodies, or the like. The probes may be used to identify the enzyme in other species by employing the nucleic acids for hybridization or the antibodies for identification of cross-reactive proteins.

The isolation of the AT- and other penicillin biosynthetic genes allows for the identification of regulatory elements of the individual genes such as a promoter, an upstream activating sequence (UAS), a terminator and the like. This can be achieved by sequence comparison of the genes amongst themselves and by comparison with the sequence as obtained for the isopenicillin N-synthetase biosynthetic gene and other related genes. This latter comparison, moreover, may disclose the specific nature of the regulation of the gene expression of the group of penicillin biosynthetic genes.

Identification of such a "penicillin biosynthetic regulatory element" leads to identification of specific regulatory proteins b means of standard techniques as gel retardation, cross-linking, DNA foot-printing and the like. Isolation of the specific regulatory protein by affinity chromatography will result in the cloning of the gene encoding said protein and subsequent manipulation in a suitable host.

By use of the cloned AT-gene and other penicillin biosynthetic genes, modified enzymes may be designed and synthesized. These modifications will result in modified characteristics of the enzymes, such as a change in pH or temperature optimum, a change in stability or a change in substrate specificity. Host strains, transformed with genes encoding these modified enzymes, may be programmed to perform antibiotic synthesis under different conditions or to synthesize alternative antibiotics, e.g. ampicillin instead of penicillin.

In another aspect of the invention, the cloned genes may be used to transform host strains that do not naturally possess these enzymes. It is known that Streptomyces and Acremonium do not possess the AT-enzyme, while on the other hand Penicillium lacks the genes from the cephalosporin and cephamycin biosynthetic enzymes. Introduction of such genes into the hosts will result in biosynthesis of cephalosporin or cephamycin by Penicillin or cephalosporins with a hydrophobic side chain by Acremonium.

The following examples are offered by way of illustration and not by way of limitation.

EXPERIMENTAL

EXAMPLE 1

Construction of a genomic library of Penicillium chrysogenum

A genomic library of *Penicillium chrysogenum* (ATCC 28089) was constructed in substantial accordance with methods known in the art (T. Maniatis et al., (1982) *Molecular cloning*: A Laboratory Manual, Cold Spring Harbor Laboratory, (N.Y.). Chromosomal DNA was extracted from *Penicillium chrysogenum* by forming protoplasts from the mycelium as previously described in EP-A-260762.

The protoplasts were then lysed by diluting the isotonic (0.7 M KCl) suspension with four volumes of TES buffer (0.05 M Tris-HCl pH 8.0, 0.1 M EDTA, 0.15 M NaCl). To the lysate, 1% sodum laurylsulphate was added and the mixture was incubated at 55° C. for 30 min. After one extraction with phenol and two extractions with chloroform, the DNA was precipitated with ethanol, dried, and dissolved in TE buffer (10 mM Tris, 1 mM EDTA pH 8.0). The DNA solution was then treated with 100 μg/ml RNase at 37° C. for 1 hr and subsequently with 200 μg/ml proteinase K at 42° C. for 1 hr. The solution was extracted once with phenol and twice with chloroform. An equal volume of isopropanol was layered on top of it and the DNA was collected at the interface by spooling around a glass rod. After drying, the DNA was dissolved in TE buffer. The molecular weight of the DNA preparation thus obtained was about $10^8$ EDal. The DNA was partially digested with Sau3A ligated to dephosphorylated EMBL3 arms cut with BamHI (Promega Biotec, Madison Wis.), and packaged into bacteriophage lambda capsids using the Packagene System of Promega Biotec. All reactions were carried out in accordance with the manufacturer's recommendations except that the packaging reaction was carried out at 22° C. for 2-3 hours. Libraries were amplified by plating the packaged phages, incubating for 7-8 hours at 37° C. and eluting the phages using 4 ml of SM buffer (0.1 M NaCl, 0.01 M MgSO$_4$, 0.05 M Tris-HCl pH 7.5, 0.01% gelatin) per Petri plate.

EXAMPLE 2

Isolation of genes specifically expressed during penicillin biosynthesis using a differential screening procedure Genes that are specifically or predominantly expressed during penicillin biosynthesis were identified by probing the genomic library of Example 1 with labelled cDNA probes synthesized on mRNA templates extracted from producing (lactose-grown) and non-producing (glucose-grown) mycelia, and selecting the clones that gave a positive signal with the former (+) probe only.

Messenger RNAs were isolated from cultures grown 3 or 6 days in the production medium (cf. Example 1) (+preparation) or in the same medium with the lactose replaced by glucose (−preparation). The mycelia were collected by filtration, frozen in liquid nitrogen, homogenized and the mRNA isolated using the guanidinium isothiocyanate method as described by T. Maniatis et al., (vide supra).

cDNAs were synthesized and labelled to a high specific activity with [α-$^{32}$P] dATP against both mRNA populations in a reaction mixture of 30 μl containing

| 12.5 | mM | MgCl$_2$ |
|---|---|---|
| 50 | mM | Tris-HCl pH 8.3 |
| 100 | mM | KCl |
| 125 | mM | DTT |
| 2 | u/μl | RNasin |
| 500 | μM | dGTP |
| 500 | μM | dCTP |
| 500 | μM | dTTP |
| 25 | μM | dATP |
| 0.1 | μg/ml | BSA |
| 100-200 | μg/ml | poly A$^+$RNA |
| 50-60 | μg/ml | oligo dT$_{12-18}$ |
| 1.2 | u/μl | reverse transcriptase |
| 1.67 | μCi/μl | [α-$^{32}$P] dATP | in which the PolyA+ RNA and oligo-dT were mixed separately, heated to 100° C. for 1 minute, and cooled in ice water prior to adding to the reaction mixture. After 1.5 hrs incubation at 42° C., 5 μl of 1 mM dATP was added and the incubation continued for 30 min. Subsequently, the reaction mixture was made 20 mM in EDTA, 40 mM in NaOH (final volume 100 μl) and heated to 65° C. After 1 hr incubation, 5 μl M Tris-HCl pH 8.3, 40 μl 0.1 N HCl, 7 μg calf thymus DNA, 100 μl TES buffer (10 mM Tris, 1 mM EDTA, 1% SDS pH 7.5) and 200 μl 5M ammonium acetate were added and the DNA was precipitated with 800 μl ethanol for 16 hrs at −20° C.

The precipitate was collected by centrifugation, washed with 70% ethanol, dried, and dissolved in 32.5 μl of TE buffer (10 mM Tris, 1 mM EDTA pH 8.0). The (+) cDNA preparation was then enriched for sequences specifically expressed during penicillin biosynthesis by two successive rounds (cascades) of hybridization against a (−) mRNA preparation in a reaction mixture of 75 μl containing

| 32.5 μl | (+) cDNA |
|---|---|
| 10 μl | (−) mRNA (1 μg/μl) |
| 30 μl | 1 M NaPO$_4$ pH 6.8 |
| 1.5 μl | 10% SDS |
| 1 μl | 0.5 M EDTA |

After incubation for 16 hrs at 68° C., 102 μl of water was added (final phosphate concentration 170 mM) and the mixture passed through an hydroxylapatite column equilibrated in 170 mM phosphate at 68° C. Under these conditions, double stranded nucleic acids bind to the column whereas single stranded nucleic acids are eluted. The eluate was collected, dialyzed against TE buffer for 1.5 hrs, and ethanol precipitated after addition of 4 μg carrier (calf thymus) DNA. This procedure was repeated and the final unbound cDNA was directly used as a probe to screen a genomic library of a high-producing Penicillium strain as follows:

A sample of the amplified library of Example 1 was plated onto 5 Petri plates so as to contain approximately 1500 plaques per plate. The plaques were transferred in duplicate to Gene Screen Plus filters (New England Nuclear) according to the manufacturer's recommendations. One set of filters was probed with labelled (+)cDNA preparation; the duplicate set was probed with the (−)cDNA as a control.

Positive plaques were purified and subjected to a second screening. In this way, 96 plaques were selected that gave a positive signal with the (+)cDNA probe only.

DNAs of recombinant phages that had given a strong or moderate signal in the initial screening were labelled with $^{32}P$ and used as probes to screen Northern blots of Penicillium RNAs isolated from producing and non-producing mycelia, in order to establish the levels of expression under both conditions. In this way the recombinant clones were divided into three groups:

Class 1 contains genes highly expressed during penicillin biosynthesis and is exemplified by clones

| |
|---|
| * G2 and B21 |
| * B9, L5 and G5 |
| * L12 |
| * K9 |

Class 2 moderately expressed, exemplified by

| |
|---|
| * C12 |
| * P3 and K11 |
| * B13 |
| * B20 |

Class 3 weakly expressed, exemplified by

| | |
|---|---|
| * G3 | * L18 |
| * G1 | * K16 |
| * L10 | * B23 |

Physical maps of these recombinant phages are shown in FIGS. 2a and 2b. Clones G2 and B21 gave a positive hybridization signal when probed with an isopenicillin N-synthetase-specific probe (Samson et al., vide supra). Surprisingly, the same clones appeared also to hybridize to an acyltransferase-specific probe (see Example 5).

The promoter regions of genes isolated in this way are used to direct efficient expression of genes under penicillin-producing conditions.

EXAMPLE 3

Purification of acyltransferase

Penicillium chrysogenum strain (ATCC 28089) was inoculated (at $2 \times 10^6$ conidia/ml) in a complex seed medium containing: corn steep liquor (20 g/l); distiller solubles (20 g/l); sucrose (20 g/l); CaCO$_3$ (5 g/l) (pH before sterilization 5.7). After 36 hrs incubation at 25° C., 250 rpm, the obtained culture was used to inoculate twenty volumes of complex production media containing: Corn steep solids (35 g/l); lactose (25 g/l); potassium phenylacetate (2.5 g/l); MgSO$_4$.7H$_2$) (3 g/l); KH$_2$PO$_4$ (7 g/l); corn oil (2.5 g/l); CaCO$_3$ (10 g/l). After continuation of the incubation for another 48 hrs, the mycelium was collected by filtration and the filter cake washed four times with cold 0.15 M NaCl.

200 grams (wet weight) of mycelium were suspended in 700 ml of 0.05 M Tris-HCl buffer (pH 8) containing 5 mM dithiothreitol (hereinafter referred to as TD buffer) and disrupted in a Braun desintegrator (Braun, Melsungen, F.R.G.) using Ballotini glass beads (Sigma type V, diameter 450–500 μm) for periods of 30 s at intervals of 15 s with refrigeration in an ethanol/dry ice bath. The extract was then centrifuged for 30 min. at $20,000 \times g$. This and all following steps were carried out at 4° C. To 640 ml of the extract, 27 ml of a 10% w/v protamine sulfate solution in 0.05 M Tris-HCl pH 8 was slowly added. After stirring the mixture for 45 min., the nucleic acid precipitate was removed by centrifugation at $20,000 \times g$ and the supernatant fractionated by precipitation with ammonium sulfate while maintaining the pH of the solution at 8.0 during the ammonium sulfate additions. The fraction precipitating between 40% and 55% saturation was dissolved in TD buffer containing 1 M ammonium sulfate and applied to a phenylsepharose CL-4B column ($1.8 \times 16$ cm) equilibrated with the same buffer. The column was washed with TD buffer at a flow of 5 ml/min until no more unbound proteins were released. Then the acyltransferase was eluted from the column with 40% ethylene glycol in 0.05 M Tris-HCl pH 8.0.

The eluted fractions were assayed for acyltransferase activity by incubating at 25° C. in a reaction mixture containing 0.2 mM phenylacetylcoenzyme A, 0.2 mM 6-aminopenicillanic acid, 5 mM dithiothreitol, 0.1 M Tris-HCl pH 8.0 and enzyme extract in a final volume of 200 μl. After 10 min., the reaction was stopped by adding 200 μl methanol. The samples were centrifuged at $5000 \times g$ and the penicillin G was assayed in the supernatant by conventional microbiological or chromatographic methods.

The active fractions from the phenylsepharose column were pooled and applied to a DEAE-Sephacel column ($1.5 \times 20$ cm) equilibrated with TD buffer and the acyltransferase activity was eluted with a linear (0–0.25 M) gradient of NaCl in TD buffer at a flow rate of 0.25 ml/min. The pooled active fractions were precipitated with 70% ammonium sulfate and the pellet dissolved in 3 ml of TD buffer and applied to a Sephadex G-75 (coarse) column ($2.6 \times 70$ cm) equilibrated with TD buffer. The acyltransferase was eluted using TD buffer at a flow of 9 ml/hr and collected in the late part of the eluted fractions as a symmetrical peak of protein corresponding to acyltransferase activity. The final purification was 258-fold.

EXAMPLE 4

Determination of the amino-terminal amino acid sequence of acyltransferase and design of the corresponding oligonucleotide probe mixtures From the enzyme preparation, obtained as described in Example 1, acyltransferase was further purified by SDS-PAGE (Laemmli, Nature (1979) 227:680) (13% acrylamide, 50 mA). A 29 kD-band (about 10 μg of protein) was cut out of the SDS-gel and the protein was electrophoretically transferred onto a PCGM-2 membrane (polybrene impregnated glassfibre, Janssen, Beerse, Belgium), using a Multiphor II Nova blot unit (LKB; 0.8 mA/cm$^2$; 90 min.; electrode buffer 5 mM sodium borate pH 8.0). After blotting, the PCGM-membrane was washed four times with 25 mM NaCl, 10 mM sodium borate, pH 8.0 and air dried.

The PCGM-adsorbed protein band thus obtained was analyzed for N-terminal amino acid sequence, using a gasphase sequenator (Applied Biosystems model 470 a). The following sequence was determined:

thr—thr—ala—tyr—cys—gln—leu—pro—asn—gly—
ala—leu—<u>gln—gly—gln—asn—trp—asp</u>

According to the underlined part of this amino acid sequence, the following sets of oligodeoxyribonucleotides were synthesized:

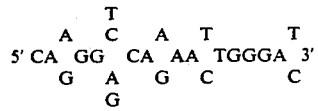

The amino-terminal amino acid sequence of a 10 kD band present in the preparation was also determined, but not used for the construction of an oligodeoxyribonucleotide probe.

EXAMPLE 5

Identification of the acyltransferase gene

The DNA of a number of the lambda clones of Example 2 was digested with restriction endonuclease SalI, the fragments separated on a 0.7% agarose gel, transferred to Genescreen Plus and hybridized to the [$^{32}$P]-end labelled oligonucleotide mixtures of Example 4. The clones giving a positive signal were mapped by restriction analysis using standard methods. Two representative physical maps derived for the recombinant phages, lambda B21 and lambda G2, are shown in FIGS. 2a and 2b. The oligodeoxyribonucleotide mixture hybridized specifically to the EcoRI/HindIII subfragment indicated on the map. This and the adjacent fragments were recloned in pTZ 18/19 (United States Biochemical Corporation) and subjected to nucleotide sequence analysis. The determined sequence and the deduced amino acid sequence are shown in FIG. 3.

The amino-terminal amino acid sequence of a 10 kD band also present in the preparation was determined and found to correspond to a DNA sequence upstream of the 29 kD sequence. Therefore, AT is probably synthesized as a 40 kD protein. This notion is confirmed by the length of the AT messenger, which was demonstrated to be 1500 bases (similar to the isopenicillin N-synthetase mRNA which encodes a 38 kD protein), allowing for 3' and 5' untranslated regions of 100 bases.

The amino acid sequences of the 29 and 10 kD proteins revealed the presence of two introns. A third intron is postulated on the basis of the gross amino acid composition of the 10 kD protein (97 residues) and on the consensus sequence for its boundaries (Ballance, *Yeast* (1986) 2:229-236).

EXAMPLE 6

Construction of a transformation vector with a high transformation efficiency

Figure 6:
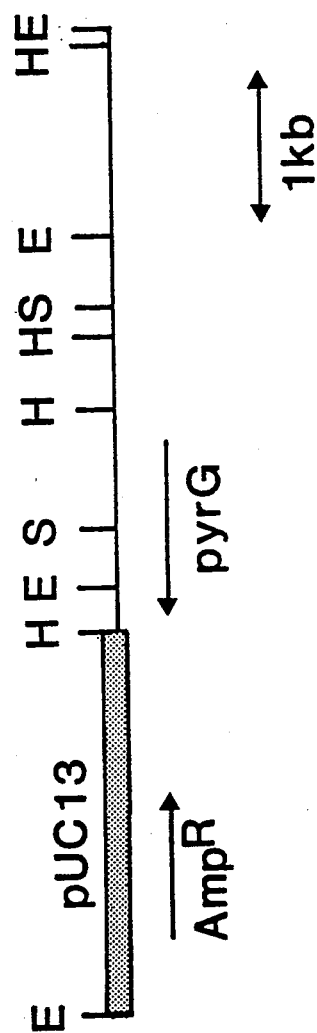
Figure 7:
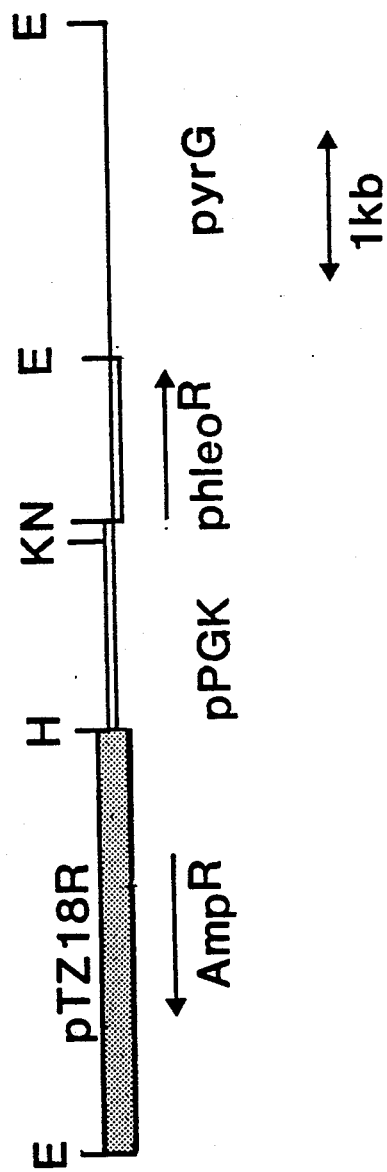
Figure 8:
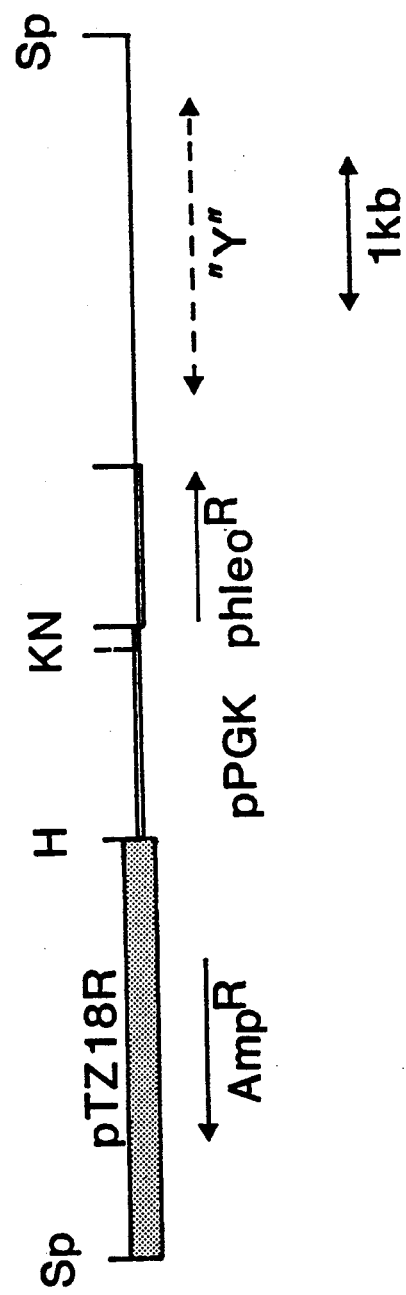
Figure 9:
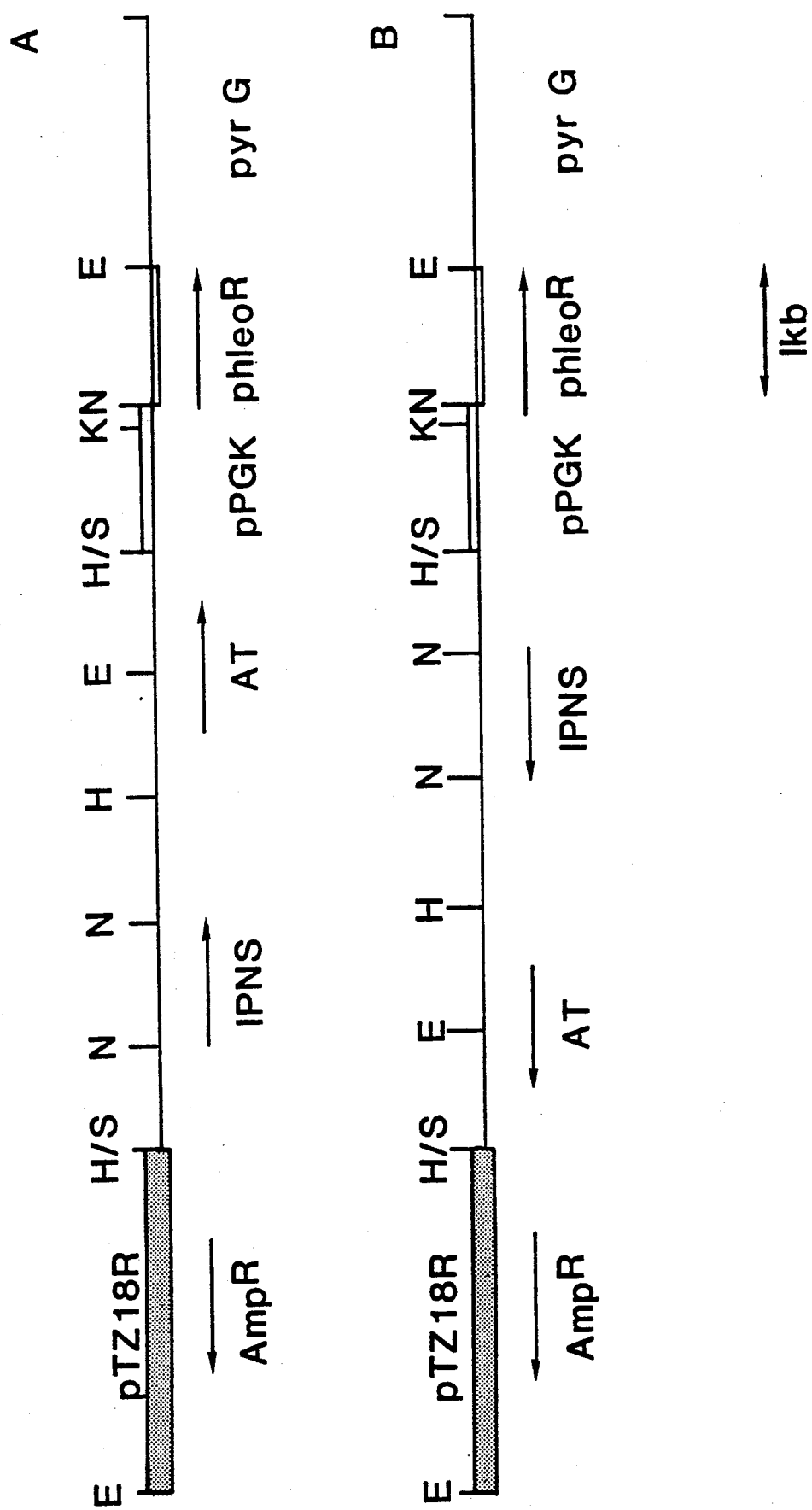
Figure 10:
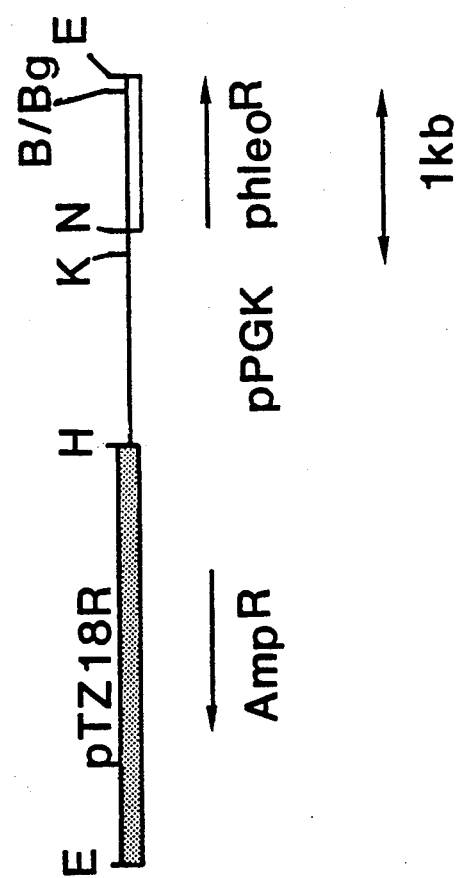

In order to obtain a transformation frequency of *P. chrysogenum* that is sufficiently high to allow introduction of genes by transformation or cotransformation with the aim of complementing or amplifying non-selectable genes involved in β-lactam biosynthesis, it is necessary to include in the transformation vector a transformation-enhancing sequence (cf. ans in *Aspergillus*, Ballance and Turner, *Gene* (1985) 36:321-331). Surprisingly, a transformation-stimulating sequence which is functional in *P. chrysogenum* is present on a DNA fragment containing the P. chrysogenum pyrG gene. Part of this 2.4 kb EcoRI fragment is specified by the nucleotide sequence shown in FIG. 4. This DNA fragment forms part of a 4 kb Sau3A partial fragment, cloned in the BamHI site of plasmid pUC13 (Messing, *Meth. Enzymol.* (1983) 101:20). This plasmid is referred to as pUC13::pyrG hereinafter (see EP-A-260762 and FIG. 6).

The 2.4 kb EcoRI fragment was included in a plasmid (pPS47) containing the phleomycin-resistance gene of *Streptoalloteichus hindustanus* under the control of the promoter of the phosphoglycerate kinase (PGK) gene from *P. chrysogenum*. This latter gene was isolated from a Penicillium genomic library by standard methods (Maniatis; Example 1), using the corresponding yeast gene (Hitzeman et al., vide supra) as a hybridization probe. The promoter region is specified in part by the sequence shown in FIG. 5, which is located directly upstream of the PGK coding region. The pyrG-containing vector is pPS54.

The stimulatory effect of the pyrG fragment on the frequency of transformation is shown in Table 1 below:

TABLE 1

| Plasmid | Transformants/µg DNA |
| --- | --- |
| pPS 47 (<u>phleo</u>$^R$) | 37 |
| pPS 54 (<u>phleo</u>$^R$, <u>pyr</u>G) | 186 |

EXAMPLE 7

Biological and biochemical verification of the identity of the AT clones

The identity of the AT clones was biologically verified by complementation of an acyltransferase-negative mutant of *P. chrysogenum* Wis 54-1255, npe 8.

2×10$^7$ protoplasts of a uracil-requiring derivative of strain Wis 54-1255 npe 8, Wis 54-1255 npe 8 pyrG (CBS 512.88), were cotransformed with a mixture of 5 µg of the selective plasmid pUC 13:: pyrG and 15 µg of lambda B21 DNA as described previously (EP-A-260762).

Several hundred transformants were obtained of which the conidia were collected and plated onto the complex production medium of Example 1 at a density of 1–10 colonies per Petri dish. After 3 days incubation at 25° C., the plates were overlayered with a spore suspension of a penicillin-sensitive *Bacillus subtilis* indicator strain and incubated overnight at 30° C. to determine the size of the inhibition zones in the bacterial lawn.

Most (75%) of the transformants showed very small haloes, the size of the penicillin non-producing recipient strain npe 8 pyrG. The remaining 25% showed large inhibition zones comparable to those of the wild-type strain, Wis 54-1255. It was concluded that the former class had received only the selective plasmid pUC 13::pyrG, whereas the latter had received both pUC 13:: pyrG and lambda B21, which restores penicillin productivity.

For several transformant clones from both groups, the level of AT-activity in cell-free extracts was determined as follows: Mycelia were collected after two days growth as described in Example 1, washed, frozen in liquid nitrogen and pulverized. For each assay, 2.5 grams of ground mycelium was suspended in 50 mM potassium phosphate buffer (pH 8.0) containing 5 mM dithiothreitol and 5 mM EDTA (final volume 12.5 ml) and stirred for 25 min. The cell-free extract was obtained by centrifugation of the suspension (5 min. at 1000×g).

AT-activity was assayed by incubating 2 ml of cell-free extract with 0.1 ml dithiothreitol (10 mg/ml), 0.2 ml 6-aminopenicillanic acid (10 mg/ml) and 0.2 ml phenylacetylcoenzyme A solution (20 mg/ml) at 25° C.

After 15 or 30 min., the reaction was stopped by adding an equal volume of methanol and the sample centrifuged (20 min. at 5000×g). The supernatant was then assayed for penicillin G by chromatographic (HPLC) methods known in the art. The results of a typical experiment are shown in Table 2 below. These data show that in transformed strains ( 3) and 4) ) the level of AT activity is increased 2-3 fold over that of the wild-type ( 5) ), consistent with the increased gene dosage.

The IPNS plus AT cluster was subcloned into pPS54, yielding pGJ01 A and B. A SalI fragment of 5 kb was made blunt by the action of T4 DNA polymerase and ligated into the unique HindIII site of pPS54, after treatment of this vector with T4 DNA polymerase.

TABLE 3-continued

| Strain | Relative production of penicillin |
|---|---|
| Wis 54-1255::pRH0-5 | 126 |

The increased gene dosage of gene Y in the transformant, as compared to the untransformed host, was confirmed by Southern blot analysis. Hence the increased gene dosage of gene Y, a cryptic gene, isolated by the method of the invention, results in a substantial increase in penicillin production.

EXAMPLE 9

Construction of pPS47

The *P. chrysogenum* PGK promoter was cloned into pTZ18R as a 1.5 kb HindIII fragment and a clone having the desired orientation was selected.

Subsequently, the phleomycin resistance gene was cloned into the BamHI site of the polylinker of this clone as a 1.0 BamHI plus BglII fragment, isolated from pUT702 (Cayla, Toulouse Cedex, France). The PGK promoter was fused in frame to the phleomycin resis-

TABLE 2

| STRAIN | TRANSFORMED WITH: | HALO: | UNITS* PEN-G FORMED PER MG PROTEIN. | | NUMBER OF AT COPIES AS ESTIMATED BY SOUTHERN HYBRIDIZATION |
|---|---|---|---|---|---|
| | | | AFTER 15 Minutes | AFTER 30 Minutes | |
| 1. Wis 54-1255 npe 8 pyrG | pUC 13::pyrG | — | passes test | 0.9 | 1** |
| 2. Wis 54-1255 npe 8 pyrG | pUC 13::pyrG plus lambda B21 | — | 1.7 | 1.1 | 1** |
| 3. Wis 54-1255 npe 8 pyrG | pUC 13::pyrG plus lambda B21 | + | 11.9 | 9.5 | 2 |
| 4. Wis 54-1255 npe 8 pyrG | pUC 13::pyrG plus lambda B21 | + | 10.8 | 7.0 | 2 |
| 5. Wis 54-1255 | not transformed | + | 4.5 | 2.7 | 1 |

*relative AT activity in extract
**inactive by mutation

EXAMPLE 8

Increased penicillin production in a host strain transformed with the cryptic gene Y To show the effect of the genes identified herein as involved in penicillin production, the gene dosage of one of these genes was increased in a Penicillium host strain. To this end the gene "Y," contained in lambda clones B9, L5 and G5, was subcloned as a 3.0 kb BamHI plus SphI fragment into pPS47. The resulting construct, pRH05 was transformed to *P. chrysogenum* Wis 54-1255 (ATCC 28089) and phleomycin resistant clones were isolated. Several clones were tested for penicillin production in shake flasks.

The results obtained for one isolated transformant are shown in Table 3 below.

TABLE 3

| Strain | Relative production of penicillin |
|---|---|
| Wis 54-1255 | 100 | tance gene, by looping out the sequence to be deleted using an oligonucleotide with the sequence:

5'-GGA ACG GCA CTG GTC AAC TTG GCC ATG GTG GGT AGT TAA TGG TAT G-3'

Moreover, this oligonucleotide introduces an NcoI site at the position of the ATG.

It is evident from the above results that secondary metabolite production can be greatly enhanced by employing screening procedures which allow for identification of DNA sequences associated with production of a secondary metabolite. By using subtraction libraries in identifying specific sequences associated with secondary metabolite production as contrasted with strains lacking such production, mRNA and cDNA may be isolated and identified for use as probes. Thus, fragments containing cryptic genes, which will not have a known function are found to greatly enhance secondary metabolite production and may be transformed into a host for production of the secondary metabolite. This procedure is specifically exemplified for penicillin.

In addition, an acyltransferase gene is provided which finds use in a variety of ways, as an enzyme for modifying β-lactam compounds, as a label, as a source of an antigen for a production of antibodies to acyltransferase, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for enhancing the production of a secondary metabolite in a bacterium or fungus host which produces said secondary metabolite, said method comprising:
   screening a DNA library prepared from a first host producing said secondary metabolite with probes obtained from mRNA or DNA derived therefrom from a second host of the same species lacking the production of said secondary metabolite;
   screening a genomic library of said first host with sequences which do not hybridize to said probes to identify fragments comprising genes transcribed in said first host which are not transcribed in said second host;
   preparing DNA constructs comprising said transcribed fragments and a marker for selection;
   transforming a candidate host capable of production of said secondary metabolite with said constructs and cloning the resulting transformants; and
   identifying clones producing said secondary metabolite at a higher level than said candidate host.

2. A method according to claim 1, including the additional step of:
   screening transcription sequences of said first and second hosts with said fragments to determine the level of transcription of said gene.

3. A method according to claim 1, wherein said first and second hosts are *Penicillium, Aspergillus, Acremonium* or *Actinomycetes*.

4. A vector comprising (a) a gene encoding a protein involved in production of a β-lactam antibiotic selected from the group consisting of an acyltransferase gene, cryptic gene Y and a cryptic gene present on any of clones L12, K9, C12, P3, K11, B13, B20, G3, G1, L10, K16, and B23, (b) a marker for selection in a host producing said β-lactam antibiotic and optionally (c) a sequence for enhancing transformation efficiency of said vector in said host.

5. A vector according to claim 4, selected from the group consisting of pGJ01 A, pGJ01 B, and pRH05.

6. A vector according to claim 4, wherein said β-lactam antibiotic is a penicillin.

7. A vector according to claim 6 selected from the group consisting of pGJ01 A, pGJ01 B, and pRH05.

8. A vector according to claim 4, wherein said gene comprises other than the endogenous promoter for transcription.

9. A transformed host comprising a vector according to any of claims 5, 6, 7, 8, or 4.

10. A transformed host capable of increased expression of a β-lactam antibiotic selected from the group consisting of *Penicillium, Aspergillus, Acremonium*, and *Actinomycetes*, comprising as a result of transformation an extra copy of a sequence comprising a gene selected from the group consisting of an acyltransferase gene, cryptic gene Y, and a cryptic gene present on any of clones L12, K9, C12, P3, K11, B13, B20, G3, G1, L10, K16, and B23, and encoding a protein involved in production of a β-lactam antibiotic.

11. A transformed host according to claim 10, wherein said β-lactam antibiotic is penicillin.

12. A transformed host according to claim 10, wherein said gene is endogenous to said host.

13. A transformed host according to claim 12, wherein said β-lactam antibiotic is penicillin.

14. A transformed *Penicillium* host capable of increased expression of penicillin comprising as a result of transformation an extra copy of a sequence comprising a gene selected from the group consisting of an acyltransferase gene, cryptic gene Y, and a cryptic gene present in any of clones K12, K9, C12, P3, K11, B13, B20, G3, G1, L10, K16, and B23, and encoding a protein involved in production of a penicillin.

15. A transformed *Penicillium* host according to claim 14, wherein said host is the species *Chrysogenum*.

16. A transformed *Penicillium* host according to claim 14, wherein said gene is under the transcriptional initiation regulation of other than the wild-type transcriptional initiation regulatory region.

17. A method for providing improved yields of a β-lactam antibiotic comprising: growing a transformed host comprising an extra copy of a sequence comprising a gene selected from the group consisting of an acyltransferase gene, cryptic gene Y, and a cryptic gene present on any of clones L12, K9, C12, P3, K11, B13, B20, G3, G1, L10, K16, and B23, encoding a protein involved in production of said β-lactam antibiotic resulting in enhanced production of said β-lactam antibiotic.

18. A method according to claim 17, wherein said host is a *Penicillium, Aspergillus, Acremonium* or *Actinomycetes*.

19. A method according to claim 18, wherein said host is *Penicillium chrysogenum*.

20. A gene encoding a protein involved in production of a secondary metabolite, said gene prepared according to a method comprising (1) screening a DNA library prepared from a first host producing said secondary metabolite with probes obtained from mRNA or DNA derived therefrom from a second host of the same species lacking the production of said secondary metabolite; and (2) screening a genomic library of said first host with sequences which do not hybridize to said probes to identify fragments comprising genes transcribed in said first host which are not transcribed in said second host.

21. A DNA construct comprising (a) a gene encoding a protein involved in the production of a secondary metabolite and (b) a marker for selection in a host producing said secondary metabolite, said gene prepared according to a method comprising (1) screening a DNA library prepared from a fist host producing said secondary metabolite with probes obtained from mRNA or DNA therefrom from a second host of the same species lacking production of said secondary metabolite; and (2) screening a genomic library of said first host with sequences which do not hybridize to said probes to identify fragments comprising genes transcribed in said first host which are not transcribed in said second host.

22. A transformed host and progeny thereof capable of production of a secondary metabolite, prepared according to a method comprising transforming a candidate host capable of production of said secondary metabolite with a DNA construct according to claim 21.

* * * * *